(12) United States Patent
Dilworth et al.

(10) Patent No.: US 9,050,025 B2
(45) Date of Patent: Jun. 9, 2015

(54) SYSTEM AND METHOD FOR DETERMINING VOLUME-RELATED PARAMETERS OF OCULAR AND OTHER BIOLOGICAL TISSUES

(75) Inventors: David S. Dilworth, Ann Arbor, MI (US); Bruce E. Cohan, Ann Arbor, MI (US); Zvi Flanders, Ann Arbor, MI (US); Hannah R. Peshkin, Ann Arbor, MI (US)

(73) Assignee: Eyelab Group, LLC, Ann Arbor, MI (US)

( * ) Notice: Subject to any disclaimer, the term of this patent is extended or adjusted under 35 U.S.C. 154(b) by 556 days.

(21) Appl. No.: 12/487,143

(22) Filed: Jun. 18, 2009

(65) Prior Publication Data

US 2010/0160789 A1    Jun. 24, 2010

Related U.S. Application Data

(60) Provisional application No. 61/073,493, filed on Jun. 18, 2008.

(51) Int. Cl.
| | |
|---|---|
| *A61B 6/00* | (2006.01) |
| *A61B 3/10* | (2006.01) |
| *A61B 3/00* | (2006.01) |
| *A61B 3/12* | (2006.01) |
| *A61B 5/00* | (2006.01) |
| *A61B 5/107* | (2006.01) |

(52) U.S. Cl.
CPC ............. *A61B 3/1005* (2013.01); *A61B 3/0025* (2013.01); *A61B 3/12* (2013.01); *A61B 5/7235* (2013.01); *A61B 5/0075* (2013.01); *A61B 5/1072* (2013.01); *A61B 5/1079* (2013.01)

(58) Field of Classification Search
None
See application file for complete search history.

(56) References Cited

U.S. PATENT DOCUMENTS

| | | | |
|---|---|---|---|
| 5,321,501 A | 6/1994 | Swanson et al. | |
| 5,459,570 A * | 10/1995 | Swanson et al. | 356/479 |
| 5,465,147 A | 11/1995 | Swanson | |
| 5,856,871 A * | 1/1999 | Cabib et al. | 356/503 |
| 6,002,480 A | 12/1999 | Izatt et al. | |
| 6,276,798 B1 * | 8/2001 | Gil et al. | 351/206 |
| 6,795,199 B2 * | 9/2004 | Suhami | 356/601 |
| 7,107,092 B2 * | 9/2006 | Goldstein et al. | 600/476 |
| 7,133,547 B2 * | 11/2006 | Marcelpoil et al. | 382/129 |
| 7,233,817 B2 * | 6/2007 | Yen | 600/319 |
| 7,360,897 B2 * | 4/2008 | Kikuta et al. | 351/206 |

(Continued)

OTHER PUBLICATIONS

International Search Report for PCT/US2009/047792 dated Aug. 6, 2009.

(Continued)

*Primary Examiner* — Nicholas Evoy
(74) *Attorney, Agent, or Firm* — Brooks Kushman P.C.

(57) ABSTRACT

A system and method for determining volume-related parameters of a biological tissue, such as ocular tissue, include a light source for projecting light towards the biological tissue, a receiver for receiving light reflected from the biological tissue at two spectral wavelengths, and an image acquisition system in communication with the receiver for forming an image from the reflected light at each wavelength. A processor applies a mathematical model to the image which compares the absorption of light by the biological tissue at a selected image point at each of the two spectral wavelengths to determine the volume-related parameters, such as the relative thickness and material properties, of the biological tissue at that location.

17 Claims, 3 Drawing Sheets

(56) References Cited

U.S. PATENT DOCUMENTS

| | | | |
|---|---|---|---|
| 7,364,296 B2* | 4/2008 | Miller et al. | 351/206 |
| 7,447,408 B2* | 11/2008 | Bouma et al. | 385/123 |
| 7,609,388 B2* | 10/2009 | Arieli et al. | 356/512 |
| 7,616,319 B1* | 11/2009 | Woollam et al. | 356/451 |
| 7,653,428 B2* | 1/2010 | Goldstein et al. | 600/476 |
| 7,715,002 B2* | 5/2010 | Popp et al. | 356/300 |
| 7,865,231 B2* | 1/2011 | Tearney et al. | 600/476 |
| 8,553,219 B2* | 10/2013 | Patil et al. | 356/301 |
| 8,693,745 B2* | 4/2014 | Izatt et al. | 382/128 |
| 8,801,180 B2* | 8/2014 | Hayashi et al. | 351/206 |
| 8,823,954 B2* | 9/2014 | Xu | 356/625 |
| 8,911,089 B2* | 12/2014 | Kim et al. | 351/206 |
| 2001/0030299 A1 | 10/2001 | Shiraishi | |
| 2002/0035321 A1 | 3/2002 | Bucholz et al. | |
| 2002/0091321 A1* | 7/2002 | Goldstein et al. | 600/476 |
| 2004/0233461 A1 | 11/2004 | Armstrong et al. | |
| 2004/0233944 A1* | 11/2004 | Dantus et al. | 372/25 |
| 2005/0007603 A1* | 1/2005 | Arieli et al. | 356/601 |
| 2006/0058682 A1* | 3/2006 | Miller et al. | 600/476 |
| 2007/0179381 A1* | 8/2007 | Johansson et al. | 600/476 |
| 2007/0196007 A1* | 8/2007 | Chen et al. | 382/131 |
| 2011/0080561 A1* | 4/2011 | Hayashi et al. | 351/206 |
| 2012/0083667 A1* | 4/2012 | Isogai et al. | 600/300 |
| 2012/0188538 A1* | 7/2012 | Patil et al. | 356/301 |
| 2014/0029820 A1* | 1/2014 | Srivastava et al. | 382/131 |
| 2014/0093150 A1* | 4/2014 | Zalev et al. | 382/131 |
| 2014/0185899 A1* | 7/2014 | Zalev et al. | 382/131 |

OTHER PUBLICATIONS

International Preliminary Report on Patentability for PCT/US2009/047792, dated Dec. 29, 2010.

Extended European Search Report for EP 09767725.5 dated Apr. 3, 2014.

* cited by examiner

SYSTEM AND METHOD FOR DETERMINING VOLUME-RELATED PARAMETERS OF OCULAR AND OTHER BIOLOGICAL TISSUES

CROSS-REFERENCE TO RELATED APPLICATIONS

This application claims the benefit of U.S. provisional application Ser. No. 61/073,493 filed Jun. 18, 2008, which is incorporated by reference herein.

BACKGROUND OF THE INVENTION

1. Field of the Invention

This invention relates to a system and method for determining volume-related parameters, such as the thickness and material properties, of ocular and other biological tissues.

2. Background Art

Glaucoma is an optic neuropathy in which the most important risk factor is ocular hypertension, or elevated intraocular pressure (IOP). IOP is measured easily and reliably with the Goldmann applanation tonometer. Over time, atrophy or loss of the retinal nerve fibers occurs, and when about one half the nerve fibers are lost, characteristic defects develop in the visual field. The diagnosis of glaucoma depends on the presence of these visual field defects, which are permanent, irreversible and, once present, can worsen even with treatment. Eventually, they can coalesce and lead to blindness. The modern method of plotting visual fields, computer-automated perimetry by SITA (Swedish Interactive Threshold Algorithm), is probably near the practical limit of refinement for a test based on patient responses. Because it is subjective, reliability varies with the patient, from excellent to poor.

The optic disc is the beginning of the optic nerve. It is an oval ~1.8×1.5 mm and its surface contour consists of the neural rim surrounding a depression, or cup. It is ~1.5 mm thick, and its posterior limit is the lamina cribrosa, a connective tissue grid of pores and beams. The disc (and optic nerve) is made up of about 1.5 million retinal nerve fibers, the unmyelinated axons of the retinal ganglion cells (which die in glaucoma), glia, the central nervous system's supporting cells, and fine blood vessels and capillaries. Loss of the nerve fibers in glaucoma results in a characteristic disc atrophy, which was visualized on examination through the pupil more than 100 years ago. The challenge has long been to detect atrophy before the visual field defects occur, or once field defects are present, to detect slight additional atrophy of disease progression which indicates inadequate treatment. It is not easy to detect change in the contour of the disc surface by direct visualization or photographically because of the paucity of detail on its surface and the highly light-scattering nature of this tissue, like a bundle of optical fibers. Nevertheless, after almost 50 years, the gold standard for determining the status of the optic disc in glaucoma is still the subjective qualitative assessment of stereo photographs obtained with a fundus camera.

The fundus camera is a telescopic system. During the 1970s, efforts to measure the surface contour of the optic disc by applying photogrammetric techniques to photographic images obtained with the fundus camera were unsuccessful. The goal was not significantly advanced using the photo slit lamp, which is a microscopic system to photograph the disc with patterns projected onto its surface (Cohan B E, Multiple-slit illumination of the optic disc, *Arch Ophthalmol* 1978, 96:497-500; Graebel W P et al., Quantitating Human Optic Disc Topography, *Applications of Human Biostereometrics* (*NATO*) 1978, SPIE 166:263-267; Cohan B E et al., Comparison of photo slit lamp and fundus camera photography of the optic disc, *Arch Ophthalmol* 1979, 97:1462-4).

In the last decade, three imaging technologies have been developed and each has been the target of over 100 research studies. OCT (optical coherent tomography) and GDx (scanning laser polarimetry) have as their target the nerve fiber layer of the retina but is not currently clinically applied to the disc. HRT (Heidelberg Retinal Tomography or scanning laser ophthalmoscopy) provides images of the disc at several depths to assess its surface contour. The common current opinion of glaucoma authorities on the utility of these instruments was clearly expressed by a professor who said he doesn't use any of them clinically. "None of them have been proven superior to optic disc photos and visual field analysis for diagnosing glaucoma or following progression. The American Academy of Ophthalmology hasn't recommended that you follow your patients with one particular technology, for the same reason."—Donald Budenz, M. D. Bascom Palmer Eye Institute, University of Miami; *Ophthalmology Management*, August 2003.

DETAILED DESCRIPTION OF EMBODIMENTS OF THE INVENTION

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ aspects of the present invention.

The system and method according to an aspect of the present invention determine volume-related parameters including, but not limited to, the tissue thickness and material properties, of biological tissue, such as multiple small areas of and near the optic disc. These thickness and material property estimates are the result of one or more reflection, absorption, transmission, scattering interactions between light, the optics in the instrument, and the biological features of a particular volume of tissue. For purposes of the present invention, then, the thickness and material property estimates may be referred to as tissue volume-related parameters, wherein volume refers to the volume of the tissue (e.g., optic disc) in the vicinity of the image point.

While the system and method according to the present invention can be applied to several ocular tissues, they may be especially useful in the ocular fundus. In particular, the system and method are appropriate for the optic disc, a critical site of damage in glaucoma and one that presents uniquely challenging properties for imaging and, as such, are applied herein to this tissue. The system and method according to an aspect of the present invention can detect small changes in disc tissue thickness and material properties, allowing comparison of these parameters over time for the diagnosis and management of glaucoma using standard clinical images. Of course, the system and method according to the present invention are applicable to biological tissues other than ocular tissue including, but not limited to, colon, stomach, or nasal tissues, or any tissues that can be examined laparoscopically or for which a color image can be obtained. Additionally, the assessment of non-biological materials, such as for material inspection, is also contemplated in accordance with an aspect of the present invention.

Figure 1:
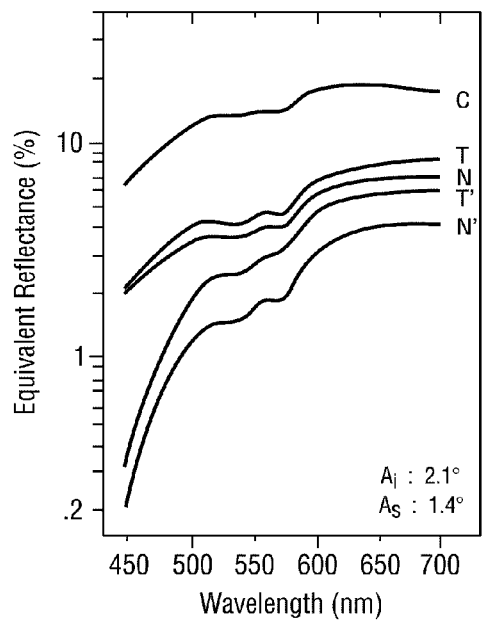
FIG. 1 is a graph illustrating the reflectance by region and wavelength of the human optic disc for the examples of a 27-year old subject (C, T, N) and a 60-year old subject (N', T')

As a reference, FIG. 1 illustrates examples of the reflectance of incident light by the optic disc as a function of wavelength and region of the disc (Delori F C, *Reflectometry measurements of optic disc blood volume*, Lambrou G N and Greve E L, eds, Ocular Blood Flow Measurements in Glaucoma, Amsterdam: Kugler & Ghedini Publications, 1989, 155-63). The curves compare the reflectance for three regions of the disc where (C) is the cup, (T) the temporal, and (N) the nasal regions in a 27 year old subject; the primed curves (T' and N') are in a 60 year old subject. Spatially, reflectance decreases with increasing tissue thickness, such that the T and N regions, which are thicker than the C region, show less reflectance. Spectrally, reflectance increases with increasing wavelength. Directly observed, the disc has a red tint except in its thinnest region (bottom of the cup). These spatial and spectral trends provide a basis for the method for tissue thickness and material property determination according to the present invention.

The system and method according to an aspect of the present invention are discussed below with respect to determining the thickness and material properties of the optic disc. The image processing described herein uses the spectral and scattering properties of the disc, wherein the relative thickness at each pixel and the material properties at each pixel in a disc image may be computed using an exponential spectral absorption model. An active spectral imaging system may be utilized to obtain localized optical measurements of portions of the optic disc, wherein that localization is sufficient to discriminate two or more regions of the disc. The detection method according to an aspect of the present invention assumes that the tissue of the optic disc, which is made up of nerve fibers and their fine blood vessels and supporting glia, contains one or more spectral signatures that are related to the local thickness and material properties. The active imaging system illuminates a small region of the disc with a light source and then image light is reflected to a two or more color (multispectral or hyperspectral) receiver where the optical signals are measured. Although the individual received signals or simple combinations of signals provide useful thickness and material property estimates, signal processing may be used to improve the spatial, spectral, and temporal determination of the localized optic disc tissue thickness and material properties. The signal processing may include, but is not limited to, contrast and brightness enhancement, matching of spectra to libraries manipulating sums, differences, products, ratios of two or more spectral signals, and scattering and volumetric models as described further below.

According to an aspect of the present invention, a model for determining volume-related parameters of biological tissue, such as optic disc tissue, is provided. The spectral characteristics of light are altered as it propagates through disc tissue, and the model assumes the disc absorption is an exponential function of thickness. The model has an incident light path through the ocular media to the disc, where it is absorbed and scattered, reflected from the lamina cribrosa, and propagated back through the disc and ocular media to the camera. The model is as follows:

$$V_M = V_O + L_I cs\rho e^{-2\alpha(d_o+d)}$$

Where:
$V_M$ measured spectral signal
$V_O$ spectral camera offset (below we assume $V_O$ has been corrected, and $V_O=0$)
$L_I$ incident spectral light
c spectral response of the camera and all other light path components
s lumped spectral and depth scattering factor of the optic disc material (including multipath and other scattering effects)
$\rho$ spectral reflectance of the lamina cribrosa region
$\alpha$ lumped spectral absorption coefficient of the optic disc material (blood is one of the parameters in the spectral absorption)
$d_o$ minimum tissue depth of the disc
d local additional tissue disc depth at each image point (d=0 at the minimum tissue depth)

With $V_O=0$ we have the measured signal at any point $$V_M = L_I c s_{(d_o+d)} \rho e^{-2\alpha(d_o+d)}$$

For the special case of d=0 we have $V_N$, the normalizing value for an image:

$$V_N = L_I c s_{(d_o)} \rho e^{-2\alpha(d_o)}$$

Dividing $V_M$ by the normalizing value $V_N$, we have:

$$y = \frac{V_M}{V_N} = \frac{L_I c s_{(d_o+d)} \rho e^{-2\alpha(d_o+d)}}{L_I c s_{(d_o)} \rho e^{-2\alpha(d_o)}} = \frac{s_{(d+d_o)} e^{-2\alpha(d_o+d)}}{s_{(d_o)} e^{-2\alpha(d_o)}} = s' e^{-2d\alpha}$$

Where $$s' = \frac{s_{(d_o+d)}}{s_{(d_o)}}$$

is a scattering factor that normalizes scattering effects at $d_o$. We have two cases for s':
1) For point source illumination, light scatters away and $s' \leq 1$.
2) For broad area illumination, light will also scatter in from other areas, and $s' \approx 1$. The $e^{-2d\alpha}$ term is exponential spectral absorption.

For two spectral wavelengths, $\lambda_1$ and $\lambda_2$, we have:

$$y_1 = s'_1 e^{-2d\alpha_1}$$

$$y_2 = s'_2 e^{-2d\alpha_2}$$

Taking the natural logarithm of $y_1$ and $y_2$ we have:

$$z_1 = \ln(y_1) = \ln(s'_1 e^{-2d\alpha_1}) = \ln s'_1 - 2d\alpha_1$$

$$z_2 = \ln(y_2) = \ln(s'_2 e^{-2d\alpha_2}) = \ln s'_2 - 2d\alpha_2$$

The difference of these values is given by:

$$\Delta z_{12} = z_1 - z_2 = [\ln s'_1 - 2d\alpha_1] - [\ln s'_2 - 2d\alpha_2]$$
$$= \ln s'_1 - 2d\alpha_1 - \ln s'_2 + 2d\alpha_2$$
$$= (\ln s'_1 - \ln s'_2) + (2d)[\alpha_2 - \alpha_1]$$
$$= \Delta \ln s'_{12} + 2d\Delta\alpha_{21}$$

Where:
$\Delta \ln s'_{12} = \ln s'_1 - \ln s'_2$, the normalized differential logarithmic scattering.

The individual terms have been normalized for $d_o$, but have a residual scattering factor that is a function of d. The $\Delta \ln s'_{12}$ term is the differential scattering between $\lambda_1$ and $\lambda_2$ over distance d.

$\Delta \alpha_{21} = \alpha_2 - \alpha_1$, the differential spectral absorption between $\lambda_2$ and $\lambda_1$, which can provide a determination of the thickness of the tissue.

The value of $\tau = 2d\Delta\alpha_{21}$, the product of the additional tissue depth and differential absorption in a localized region:

$$\tau = 2d\Delta\alpha_{21} = \Delta z_{12} - \Delta \ln s'_{12}$$

The model assumes blood is the dominant absorption factor in the disc tissue, and thus we refer to τ as tissue thickness, in arbitrary units. It is a distance measure that is scaled by differential absorption as the light scatters through the optic disc tissue, wherein the scattering is localized to a volume originating at each imaging point on the disc.

The current processing makes these simplifications:
$\Delta \ln s'_{12} \approx 0$, differential spectral scattering is set to 0.
Thus, it is assumed that scattering effects are the same for both colors at each point.
With these simplifications we have:

$$\tau \approx \Delta z_{12} - 0 = z_1 - z_2 = \ln(y_1) - \ln(y_2) = \ln\left(\frac{V_{M1}}{V_{N1}}\right) - \ln\left(\frac{V_{M2}}{V_{N2}}\right)$$

$$\tau \approx \{\ln(V_{M1}) - \ln(V_{M2})\} + \{\ln(V_{N2}) - \ln(V_{N1})\}$$

The first two terms are measured for each image pixel. The second two terms are constants for each image and estimate the measured signals when the disc tissue depth is $d_o$ (i.e. d=0). Any noises estimating these combined constants will create an offset for all τ values, and could yield computed values where d<0.

The $d_o$ point was selected for convenience as the thinnest point. A different normalization point for $d_o$ could also be selected. Selection of a different point may change the values expected for s' and other factors.

Finding the ratio of the two absorption factors provides a determination of the material properties of a particular area of the tissue. For two colors we have measured V values, and quantities that can be computed:

$$y_1 = \frac{V_{M1}}{V_{N1}} = s'_1 e^{-2d\alpha_1} \rightarrow z_1 = \ln(s'_1 e^{-2d\alpha_1}) = \ln s'_1 - 2d\alpha_1$$

-continued $$y_2 = \frac{V_{M2}}{V_{N2}} = s'_2 e^{-2d\alpha_1} \rightarrow z_2 = \ln(s'_2 e^{-2d\alpha_2}) = \ln s'_2 - 2d\alpha_2$$

The ratio of $z_1$ and $z_2$ is $$\frac{z_1}{z_2} = \frac{\ln s'_1 - 2d\alpha_1}{\ln s'_2 - 2d\alpha_2}$$

Recall $$s' = \frac{s_{(d_o+d)}}{s_{(d_o)}}$$

models the signal level effects of scattering beyond $d_o$.

Light scattered away from a point would yield s'≤1. For the case of broad area illumination, we assume the amount scattered away from a point is equal to the amount scattered into a point. Hence s'≈1 and ln(s')=0.

$$\frac{z_1}{z_2} \approx \frac{0 - 2d\alpha_1}{0 - 2d\alpha_2} = \frac{\alpha_1}{\alpha_2}$$

This alpha ratio can be used to compute the absorption properties at an image point and help identify different types of materials with different properties, such as pores, beams, arterial or venous blood vessels, degradation of the disc, etc.

Therefore, for the same local region, two or more colors may be processed in such a way that the spectral absorbance is used to estimate the localized tissue thickness, τ. The alpha ratio characterizes material properties, allowing one to distinguish between various components of the optic disc including venous and arterial blood vessels, nerve fibers, glia, and lamina cribrosa. In accordance with an aspect of the present invention, these dual parameters can be used for a single image assessment of disc condition. For example, if the thickness computation showed a thinning of a portion of the disc rim, the alpha ratio computation can augment the assessment. Conversely, if the alpha ratio is abnormal, the thickness parameter could similarly be used to support the assessment. Furthermore, the assessment of the optic disc using the thickness and alpha ratio parameters obtained from a single image can be enhanced by comparing that image to a database of images of normal and abnormal discs, optionally matched for age and demographics. A time series of images of the same disc for thickness and alpha ratio processing would facilitate the earlier diagnosis and more precise management of glaucoma via change detection, and will also detect changes due to normal aging. The time series analysis can also use database, multiple ratios, and multispectral and hyperspectral analyses. Both the analysis of single images and time series as described herein will allow earlier detection and refined management of glaucoma than current clinical practice.

The model described herein partially includes the effects of scattering. Alternatively, a model may be used that more completely takes into account the multiple scattering and absorption events. The disc tissue scatters light from one region to other regions, and this light scattering can create a "cross-talk" effect from one region to other regions, which may either help or impede the thickness and material property estimates of localized regions due to non-localized signals. By combining two or more measurements of this scattering, estimates of the "cross-talk" can be computed and corrections for it developed. These measurements and estimates may include, but are not limited to:

1) While exposing a primary region A of the disc to the localized light source, collect reflected light from region A, and also from some or all secondary regions of the disc. These secondary regions may be larger, smaller, or the same size as the region being exposed and imaged.
2) Repeat this for some or all possible primary and secondary regions of the disc.
3) The localized light source could also be illumination spots (e.g., from the slit lamp light source) ranging in size from much smaller than the disc to larger than the disc.
4) After collecting these data from these regions, develop estimates of cross-talk, and apply these to correct the thickness and material property models The estimates of cross-talk developed from the primary and secondary regions can characterize the localized scattering properties of the optic disc. These, by themselves, or in conjunction with the thickness and material property estimates are indicative of the health status of the optic disc tissue.

Although this model is applied to all pixels, where blood vessels dominate the signal in a given pixel, a tool may be provided for the manual or automatic removal of blood vessels. The current camera acquires red, green, and blue bands, and the current processing uses red and green bands. Therefore, the system and method according to an aspect of the present invention only require two colors to obtain the thickness and alpha ratio parameters described above, but it is understood that the system and method are not limited to the use of only two spectral wavelengths. Additional colors could be used to improve the thickness and alpha ratio estimates and likely develop and refine other estimates. In considering image processing techniques (binary and edge detection), inclusion of the blue band may be helpful for detecting blood vessels. Models based on the more precise spectral signatures of the disc tissue components (nerve fiber, lamina cribrosa, blood, etc.) may yield additional information on the tissue thickness and material properties.

Figure 2:
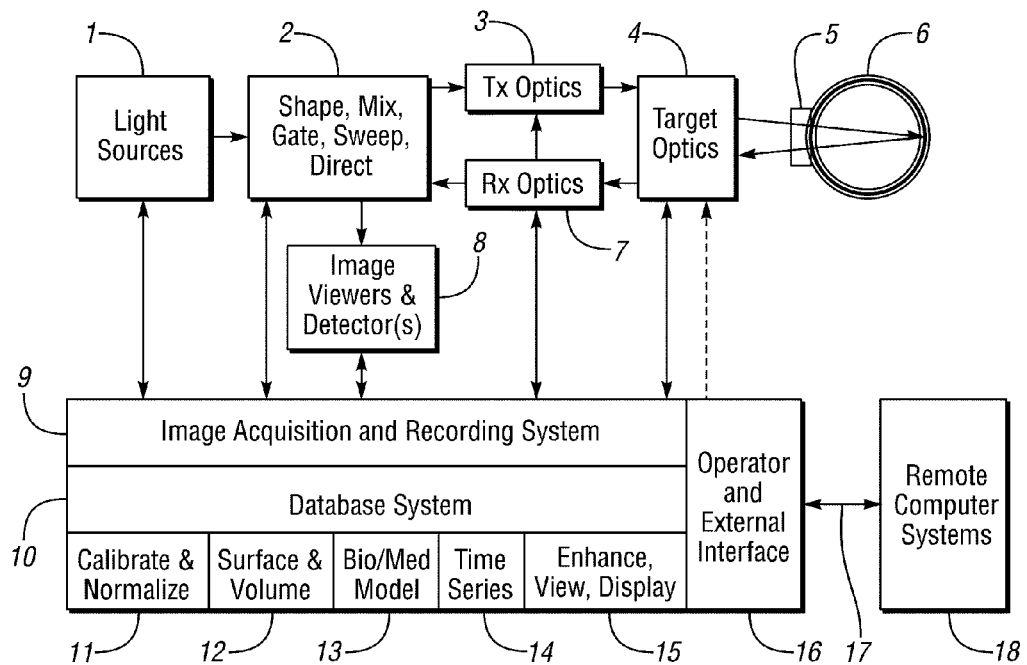
FIG. 2 is a block diagram of a system according to an aspect of the present invention for determining volume-related parameters of biological tissue.

With reference now to FIG. 2, a block diagram is illustrated of a system according to an aspect of the present invention for determining the thickness and material properties of optic disc tissue which may utilize the above model. While several subsystems are depicted in FIG. 2, it is understood that not all subsystems are required to be present for achieving the thickness and material property determinations in accordance with the present invention. For ocular image acquisition, broad spectrum light from a light source(s) 1 may be optically shaped by various optics 2, 3, and 4 before the light is projected towards local object optics 5 and the object of interest 6, in this case an in vivo human eye. The projected light may be further shaped by the local object optics 5 to improve the quality of focus inside the eye 6. Light reflected from ocular tissue 6 may be encoded with optical information that is related to the shape, thickness, and material properties of the optic disc tissue and the lamina cribrosa. Encoded information is also affected by transmittances, reflections, and absorptions of the eye 6. This collected light, which includes many types of interactions (reflection, scattering, etc.) with the optic disc tissue, is referred to herein as reflected light.

With continuing reference to FIG. 2, the reflected light passes through target optics 4, receive (Rx) optics 7, and optics block 2 and is directed to image viewers and detectors/receivers 8. This light forms images (or transforms of images) that can be viewed through eyepieces (e.g., mono or stereo microscope), on film camera(s), or with electronic camera(s) and display(s) in blocks 8 and/or 15. A digitizer may be provided to digitize the images formed. For the case of electronic cameras, the imagery can be digitized in the camera and passed to an image acquisition and recording system 9, or the camera can produce signals that are digitized by system 9. In either case, a digitized image may be acquired in system 9 where it can optionally be stored. Stored images and other housekeeping information (e.g., date, time, patient demographics, settings, gains, offsets, light source types, operators, etc.) may be stored in a database system 10 where it can be immediately processed on a host computer, accessed through another computer (e.g., remote computer system(s) 18), or processed at some time in the future by the host computers or other computers.

Processing steps according to an aspect of the present invention are shown in blocks 11-15 and carried out by a processor. The processor may be in communication with one or both of the image acquisition and recording system 9 and the database system 10 for receiving images and related data, or may be a stand alone unit configured to receive images and data for processing. The processing may include one or more of these general (unordered) processing steps:

(a) Models for transmission, reflection, absorption, and scattering of light from surfaces and within volumes;

(b) Models for spectral and polarization effects on light due to transmission, reflection, absorption, and scattering of light from surfaces and within volumes;

(c) Radiometric, spectral, and polarization calibration and signal processing;

(d) Medical knowledge of the possible shapes, depth, and volumes of the optic disc, lamina cribrosa, and related parts of the eye;

(e) Time series analysis to describe and analyze how measured and/or inferred features change over time; and (f) Statistical and related methodologies that can be applied to populations of individuals to analyze and describe how features are similar or different within the population.

According to an aspect of the present invention, these techniques may be combined with techniques developed for in vivo metrology of the eye. Imagery from the database system 10 may be calibrated and normalized in block 11. Additional techniques may include a more absolute calibration to provide better estimates about the optic disc, lamina cribrosa, and other parts of the eye. The relative surface shape and thickness may be computed in block 12 using techniques and models related to (a), (b), and (c) described above. Block 13 may apply knowledge from (d) to the previous results from blocks 8-12 to further characterize the condition of the optic disc, lamina cribrosa, and other parts of the eye. Block 14 is a specialized form of the database system 10, may apply technique (e), and may provide tools to describe and measure how the condition of the optic disc, lamina cribrosa, and other parts of the eye change over time. Techniques from (f) can be further applied to the data. The results from blocks 8-14, and intermediate steps within these blocks, can be enhanced and displayed in block 15. The displays in block 15 may include:

(a) Display of the imagery from blocks 8-14, and intermediate steps. These displays may include 2D and 3D renderings, including displays that show how imagery changes over time.

(b) Contrast and enhancement techniques to alter the appearance of displayed imagery.

(c) Texture mapping to superimpose imagery onto 3D models with different viewing perspectives, lighting, surface properties, etc.

(d) Tools to also display numerical values from blocks 8-14, and intermediate steps, with or without image displays.

In addition to storing various types of imagery, the database system 10 may also store data files, some of which are closely related to a particular image, some of which are related to groups of images, and some of which are general files that support the overall process and may not have specific relationships with image files. One or more relational databases may be used to describe the relationships between image and non-image files. The system depicted in FIG. 2 may contain one or more computers, operating systems, and a mixture of commercial and custom software.

Although blocks 1-16 could be a self-contained system, results and intermediate results can optionally be transmitted using a communications link 17 to one or more remote computers 18. In addition to remote computers 18 providing the same capabilities as blocks 1-16, the remote computers 18 could also provide additional, centralized processing capabilities, including archiving, backup, more extensive processing and database, etc.

Still referring to FIG. 2, each of blocks 1-16 will now be described in further detail with reference to the system and method for determining volume-related parameters of biological tissue according to an aspect of the present invention. One or more light sources 1 may be utilized, each with suitable radiometric, spectral, spatial/spectral coherence, polarization, and temporal properties. The radiometric and spectral properties should yield a useful signal after being acquired by the image viewers and detectors 8 and the image acquisition and recording system 9. Coherence and polarization properties may provide additional signals, but may also require additional processing (to extract information or to manage artifacts). Light sources 1 may include a flash lamp or an incandescent lamp, optionally with a filter that increases the blue to red ratio. One or more laser or LED colors may also be used.

Block 2 inputs light from light sources 1, shapes light transmitted to transmit (Tx) optics 3 and received from Rx optics 7, and may linearly or non-linearly optically mix light from Rx optics 7 with light from the light sources 1 and/or Tx optics 3. Changing the shape (diameters, angles, optical properties) at the light sources 1, Tx optics 3, and Rx optics 7 will optimize the performance of the instrument. A gate may provide a means for pulsing the illumination or imaging. The sweep may be a means for adjusting the properties described with reference to light sources 1.

Block 2 may include a Haag Streit photo (HSP) slit lamp (e.g., 900P-BQ), wherein a region slightly larger than the optic disc may be illuminated and imaged and multiple images may be rapidly acquired. Block 2 may also include a Zeiss fundus camera (ZFC) (e.g., VISUPAC and FF 450$^{plus}$), where a region of the fundus including the optic disc is imaged and multiple images are rapidly acquired. Another possibility is to illuminate and image one or more regions smaller than the optic disc, adapt a fundus camera, or integrate a spectrometer for a photo slit lamp or fundus camera. Still further, a four or more channel spectrometer could be utilized, possibly with some imaging capabilities. The spectrometer format could be a single pixel, a line, or an area. Whatever the format, the spectrometer could be aligned such that it measures the region of interest of the optic disc. The imaging may help identify the particular region of the optic disc that is being measured. The region of interest could be an area larger, equal to, or smaller than the optic disc.

The Tx optics 3 alters the optical properties of the light from block 2 to make it compatible with the target optics 4. The target optics 4 transmits light into the object of interest 6 and receives light from the object of interest 6. Local object optics 5 includes the examining contact lens (fundus or gonio for anterior chamber angle) which is in physical contact with the object of interest 6. The object of interest 6 could be a biological eye, a surrogate (model) of a human eye, or some other biological or surrogate target. Local object optics 5 provides optical corrections for the object of interest 6 and may include:

(a) An index matching fluid for the coupling of light in and/or out of the object of interest 6;

(b) An anti-reflection coating to improve the coupling of light between the target optics 4 and the local object optics 5;

(c) Shaping, polarizing, spectral filtering of the beam (e.g., a lens) to improve the image quality of the object of interest 6.

With continuing reference to FIG. 2, Rx optics 7 collects and shapes light from target optics 4. A camera may be split between blocks 8 and 9, with detectors in block 8 and acquisition in block 9. More specifically, one or more viewers or recorders 8 may be used for alignment or recording images of some, or all, of the light from the object of interest 6. The image viewers include direct viewing (e.g., slit lamp microscope or fundus camera eyepieces) or imagery from electronic camera(s) that are viewed on electronic displays. The image recorders could include film cameras, or analog or digital electronic cameras. The electronic cameras may output analog image signal(s), or the cameras may include a digitizer that is accessed immediately or that can be stored (see also block 15 description below). A three-color electronic camera (see block 9 description below), a film camera, or two (or more) color electronic camera, or an imaging spectrometer, possibly with tens or hundreds of colors may be utilized.

Blocks 1-4, 7, and part of 8 may use a modified HSP slit lamp (e.g., model number 900P-BQ), wherein modifications to the photo slit lamp may include adding an 80B color filter to the transmit path to alter the color balance, and adding a color digital camera (see block 9 description below) for imaging. A ZFC (e.g., VISUPAC and FF 450$^{plus}$ Megavision Color Camera (color filter array)) may also be utilized.

An image acquisition and recording system 9 acquires and records data from the imagery of block 8. Signal levels during imaging are important, as too much light saturates the sensor and produces non-linear signals, whereas too little light degrades image quality. With a film camera, steps include exposing the film, developing the film, scanning the film image into a computer compatible format, and inputting the scanned imagery into the computer. With an analog electronic camera, steps may include digitizing the signals (imagery and controls) from an electronic camera and storing values in computer memory. With a digital electronic camera, steps may include inputting the digitized imagery from the electronic camera and storing values in computer memory, with the input through a wired connection, a wireless connection, a removable memory card, etc.

In different implementations of blocks 8 and 9, either the ZFC or a modified HSP slit lamp may be used. Color cameras based on color filter array (CFA) technology are common, and may require special processing to extract a usable color image. The ZFC with a Megavision color CCD acquires the imagery using the established clinical acquisition procedures. The HSP slit lamp is adapted to use a Micropix 640×480 color CCD camera with a firewire interface. The instrument control software may provide the operator a means to control the exposure time and gain for each camera color, and also a means to monitor the signal levels in an operator controlled region of interest (ROI). Imagery may be displayed live (see block 15 description) and the operator may make exposure and gain settings during image acquisition. A single key stroke may save the current image to disk. Additional features could include collecting imagery in continuous streams, and autoset gain and exposure settings. Access to camera memory (e.g., GigE, Cameralink, analog, etc. interface) could be provided, as could a custom electronic camera interface.

In database system 10, one or more computer files store imagery or other project related data. All image-related files may be stored with encoded filenames (e.g., date, time, subimage type, and serial number). Image-related files may be stored with different extensions (CFA, BMP, CSV, ROI, TXT, etc). Groups of files (image-related and others) may be further organized into folders. These other files may include project files, literature data, etc. (see also block 16 description below). Two major data sets (experimental conditions and processing results) may be linked through a database (such as MS Access or the like) and keyed by the image name. The database may provide user-controlled options to create joins between the data sets, allowing output of the results for processing in MS Access, Excel, or other tools. One or more relational databases (MySQL, MS Access, etc.) may be used to further describe the relationships between files and to improve handling of the data. One database could be used for data acquisition, and additional databases for processing project files, literature data, etc. Database system 10 according to an aspect of the present invention provides a means of organizing the data into related tables, defining the relationships between the tables, and merging tables in meaningful ways. The number of databases may be reduced by combining individual databases, possibly to one comprehensive database.

Referring again to FIG. 2, digitized imagery from the image acquisition and recording system 9 can be calibrated and/or normalized at block 11. Calibration converts pixel values to standard units (e.g., watts). Normalization converts pixel values into arbitrary units (not necessarily calibrated) to facilitate further computation. Typical operations may include estimating and removing the dark image offset and estimating and applying flat fielding. In one embodiment, no calibration is performed, but each pixel may be normalized using one of three methods:

(a) Find the pixel with the brightest red value, and then use the associated green and blue values as normalizing values. This can also be implemented using green or blue as the brightest pixel.

(b) Find the brightest red, green, and blue values. Since these may not correspond to a single pixel, this approach does not fit a per-pixel model.

(c) Since the normalizing values reduce to a single offset (see the mathematical model above), find an offset that produces a value of zero.

Methods (a) and (b) can create negative tissue thickness values, hence (c) may be used. The description regarding block 12 below applies method (c) individually to each image. The description regarding block 14 below discusses ways to use shared information to reconcile the offset between images.

Alternatively, the imagery could be calibrated. The calibration could be as simple as acquiring a reference image from a known reflector, or by calibrating the lamp and/or the camera. In addition, a reference feature could be found inside the eye. The reference could be a part of the ocular anatomy or even an object that is inserted into the eye (possibly as part of an intraocular surgical procedure).

Block 12 relates to tissue surface and volume. The signal in the digitized image contains localized information about the optic disc. A biomedical model may be introduced in block 13 below. Each image pixel can be processed to estimate the local disc tissue thickness and material properties using the model provided above and a normalization method (for example, see database system 10 description).

Returning to FIG. 2, block 13 represents a biological/medical model. The model of the optic disc described herein includes localized signals that carry information from light reflected from the surface of the disc, light reflected from the surface of blood vessels that are at or near the surface of the disc, and light that has undergone one or more scattering and absorption events within the disc tissue. These events include interactions with nerve fibers, blood vessels, glia, the lamina cribrosa, etc. The volume-related parameters can be computed for any pixel in the scene and provide both quantitative and qualitative information about that region of the optic disc. A cup/disc ratio estimate may be used, wherein the optic disc cup may be precisely measured at any axis using the system and method according to an aspect of the present invention. In addition to estimating the per pixel parameters, groups of these pixels can be processed (for example, by edge detection methods) to identify different regions of the disc.

The lamina cribrosa, the deep limit of the disc, is hidden by the neural rim and usually visible faintly, if at all, through the haze of the tissue at the base of the cup. The long-standing questions about changes in its contour and pores in glaucoma can be answered by the imaging system and method according to an aspect of the present invention. The current method is normalized to the computed thinnest points of the optic disc. Deeper features behind this region create anomalous measurements which can be extended to estimate the shape of the lamina cribrosa, wherein the regular pattern observed in that thinner region may correlate with its porous structure.

Dye studies—obtaining optic disc images after intravenous injection of dyes, like fluorescein, indocyanine green, Evans blue, etc.—may permit separation of the vascular from the neural elements of the optic disc and help resolve the 100-year controversy about glaucoma as to whether the damage caused by mechanical or vascular or mixed factors. The current color CCD camera is based on the common Bayer color filter array, but imaging systems with additional spectral separation capabilities (for example, three CCD cameras or spectrometers) with or even without dyes may enhance biological feature analysis.

With reference now to time series block 14 of FIG. 2, while imagery from a single session will show the health of the optic disc at that time, imagery from multiple sessions will provide statistical and trend information regarding the health of the disc. In a given series of images, changes in position of the eye relative to the camera may occur, and each image will be spatially registered.

The enhance, view, display block 15 provides a display of a raw or processed optic disc image with enhancement techniques to improve the visibility of areas of interest. Volume-related values can be displayed in a tabular format, bar charts, and as 2D and 3D images. These techniques include showing the full image, identifying a path (concentric circles, ellipses, etc.), and identifying distinct points, where examples of these techniques are given below.

The operator and external interface 16 provides ways to control and access data. The processing produces data in raw, intermediate, processed, and displayable formats. Each image may have these related files:

1. CFA or MR Image, examples of raw images from cameras.

2. BMP Image, an image file format from the CFA with enhancements.

3. ROI data, the identified ROI, optic disc perimeter, points in the concentric paths, enabled/disabled pixels.

4. CSV data, extracted results from processing: raw, intermediate, and processed data for each point specified in the ROI data file. Disabled points are interpolated based on neighbors. This file can be input and processed by spreadsheets.

5. 3DBIL Image, an image format image file for 3D viewing.

6. 3DCSV data, volume-related values for 3D viewing. These files are arranged in a disk file system using a parallel naming convention and processed by a mixture of custom and commercial tools.

An integrated tool may be utilized that manages the processing of some or all of these files.

In accordance with an aspect of the present invention, for environments where two or more computers are used to acquire and/or process data, a communications link 17 can be established, which may include a local area network (wired or wireless) or the Internet. These operations could include, but are not limited to, remote control of the computer, installing and testing new software, moving files to or from the computer, and file management (delete, copy, backup, rename, etc.).

With reference again to FIG. 2, a remote computer system 18, located separate from the data acquisition computer, may be used to store, backup and process the data. A database system may be implemented for storage of the images, tracking the session date, and data collection parameters (exposure, gain and magnification). This computer may be capable of running on contemporary operating systems and can be accessed directly or remotely. The computer can be located in the same laboratory as the data acquisition computer or can be elsewhere and connected via Local Area Network, Wide Area Network or wireless access.

In one embodiment, the system may run Microsoft Windows XP Professional Operating system, and the data storage system may be implemented using the operating system file name and file folder hierarchy. A commercially available database system such as Oracle, MS SQL Server or MySQL running on Windows XP, Linux, Macintosh OS or any of the other versions of Unix that available may also be used. The computer itself can be a commercially available computer, equipped with and appropriate networking interface, or a specialized computer system or subsystems developed to support and this, and possibly other, operations. Furthermore, a centralized database storage and processing system with a web-based interface acting as a data repository and processing center for multiple clinical sites may be utilized. In this commercial center, images may be stored, analyzed in a central location and reports may be available though central reporting on the web-based interface or may be delivered via postal delivery or e-mail.

Figure 3:
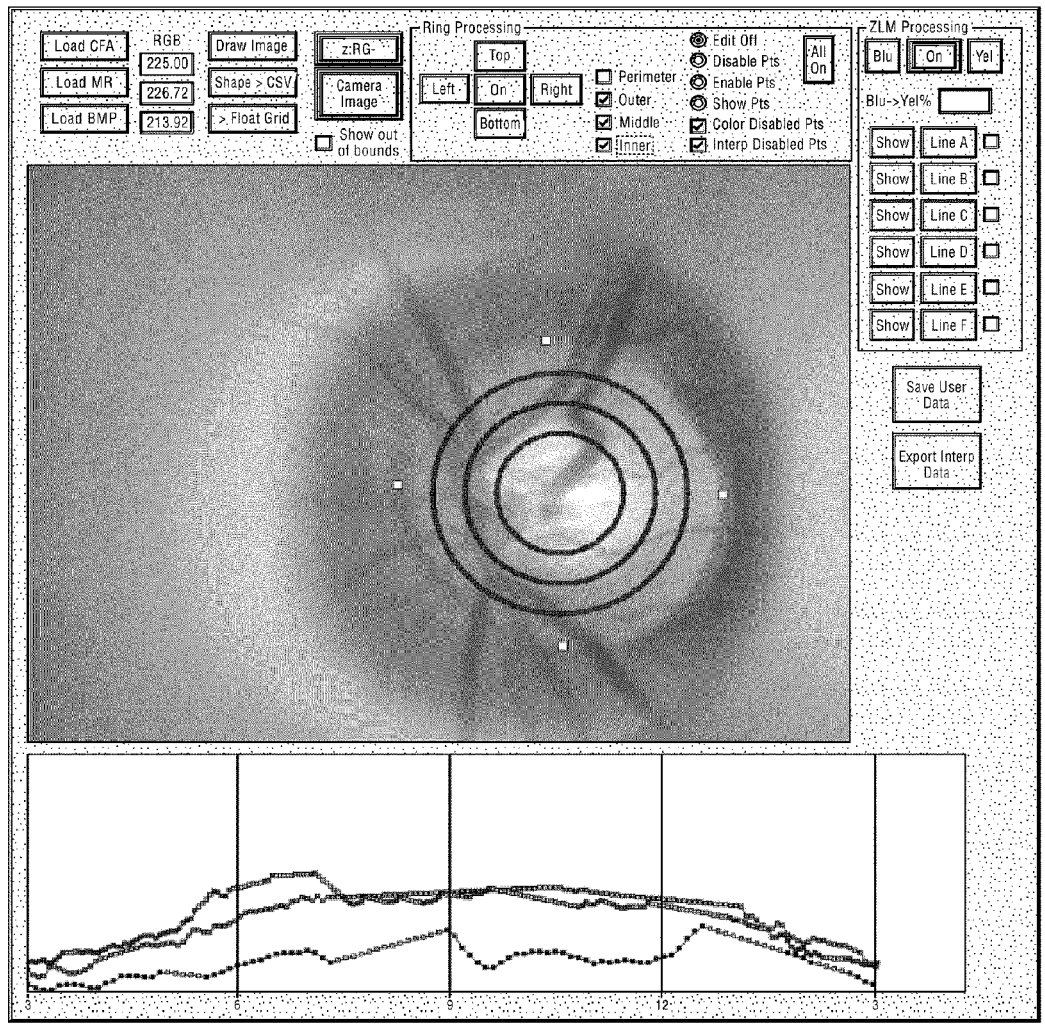
FIG. 3 is an in vivo image from a human optic disc acquired with a Haag-Streit photo slit lamp, wherein the image is displayed in a screen shot of an image processing tool according to an aspect of the present invention.

Turning now to FIG. 3, an in vivo image from a human optic disc acquired with an HSP photo slit lamp is shown, wherein the image is displayed in a screen shot of an image processing tool according to an aspect of the present invention. In the screen shot of the image processing tool, the bar at the top shows the pixel at (479, 329) having RGB values given in square brackets, intermediate results in angle brackets, and volume-related parameters after the text arrow. The 0.259 and 0.262 are two estimates of the disc tissue computed using normalization method (a) with reference to block 11 of FIG. 2.

FIG. 3 also depicts the application of a concentric circles method according to an aspect of the present invention for point-by-point comparison of multiple images. In this method, each image may be aligned to the outer edge of the optic disc by manually identifying fiducial edge points (i.e., four small white squares in FIG. 3). These points may be fit to a path, such as a circle with a computed center and radius. A plurality of concentric circles may be drawn, such as at radii of 40%, 60%, and 80% of the fit circle. The plot below the screen shot in FIG. 3 shows tissue thickness along these circular paths as an x-y plot, with x being the angular location along the path and y the local disc tissue thickness value at that point. As these paths cross vessels, individual points may be manually disabled (supervised classification). This may be accomplished by selecting from either the circular path overlaid on the photograph or the corresponding point on the plot. Once disabled, the disabled points are colored differently from enabled points. The display can show either raw pixels or values estimated based on enabled neighbors. The inner, middle, and outer lines are the 40%, 60%, and 80% circles, respectively. Yellow pixels have been disabled and are interpolated in the x-y plot. The x-axis is labeled 3, 6, 9, 12, and 3 for the clock hours. It may be possible to fit the four fiducial points to a more complex function (i.e., ellipse). In addition to concentric paths (circles, ellipses, etc.), the paths could be radial from a mid-region outward or along some other path.

Figure 4:
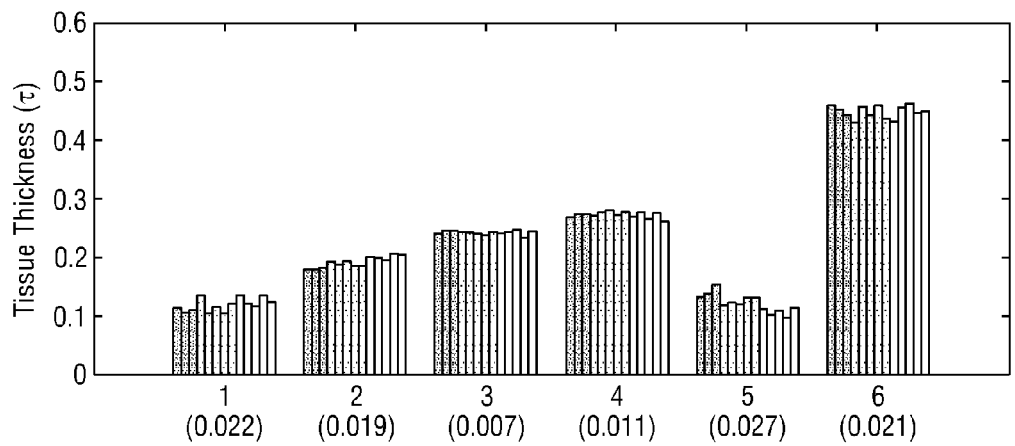
FIG. 4 is a bar chart showing repeatability of thickness computations of one optic disc on three imaging sessions, wherein the x-axis identifies the locations of points of interest on the optic disc, including thickness error given as two standard deviations, and the y-axis gives the computed thickness in each region in arbitrary units.

FIG. 4 is a bar chart showing the results from processing imagery of the optic disc of the right eye of a normal, young volunteer female subject. The chart illustrates the repeatability of thickness computations of this optic disc on three imaging sessions over a six month period (each session with different shading). The six clusters of bars each contain data from points registered in thirteen images. The x-axis identifies the locations of six points of interest on the optic disc, and the y-axis gives the computed tissue thickness in each region in arbitrary units, where the height of the bar for each point estimates tissue thickness in that region. The leftmost bar in each cluster was computed from the points mapped in FIG. 5B below, the other bars represent the other 12 images. The ±1σ variation in tissue thicknesses is given below the 1-6 labels. For this data set, assuming a full scale value of 0.6, and using an average ±1σ value of 0.018, this method resolves 33 thickness levels.

The imaging process may create unwanted height biases, where this effect is noted prior to the development of the alpha ratio model above. That effect includes two normalization terms, $\ln(V_{N1})$ and $\ln(V_{N2})$ that are "per image offsets", added to each pixel thickness value. The description of block 11 discusses three ways to estimate these offsets for each image, wherein these offsets vary from image to image and create the height biases. A "shared normalization" process may be used to partially correct for these unknown offsets. The bias does not affect the computed value of tissue thickness in a given image, rather it adds an offset to each value. The shared normalization process may include:

1. Computing the average thickness for the tissue thickness values for each image.

2. Selecting the smallest of these averages as the reference average (the maximum, average, etc. of the averages could also be chosen).

3. Computing the difference between the average and the reference average for each image.

4. Applying this difference to each bar such that the average equals the reference average for each image.

Shared normalization may reduce the ±1σ by a factor of 2× and corrects the bias terms. Shared normalization may be applied to multiple images, and this processing re-image may be individually analyzed.

Figure 5A:
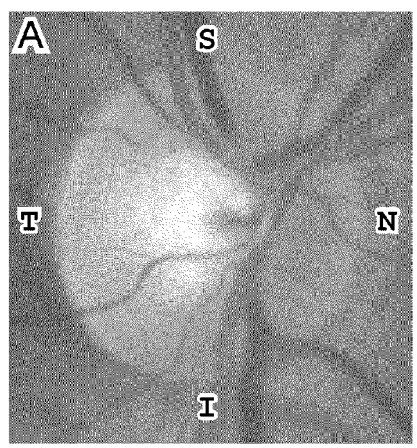
FIGS. 5A-5C depict in vivo images of a human optic disc collected with a Zeiss fundus camera, wherein the original clinical color photograph (A) is labeled for orientation (superior (S), nasal (N), inferior (I), temporal (T)) and may be used to set minimum and maximum pixel values to span the dark and bright capabilities of the display, (B) depicts a tissue thickness image computed pixel by pixel from two colors in the original color photograph, where thicker areas appear lighter and fiducial test points (i.e., 1, 2, 3, 4, 5, and 6) were located along three lines for image-to-image thickness comparisons, and (C) is a 3D perspective image that combines the color photograph with the computed thickness image, wherein the fiducial test points are shown unlabeled.
Figure 5B:
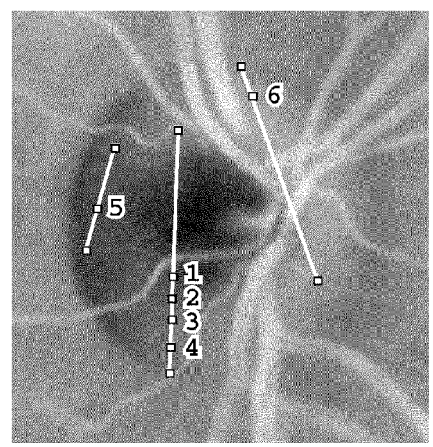
Figure 5C:
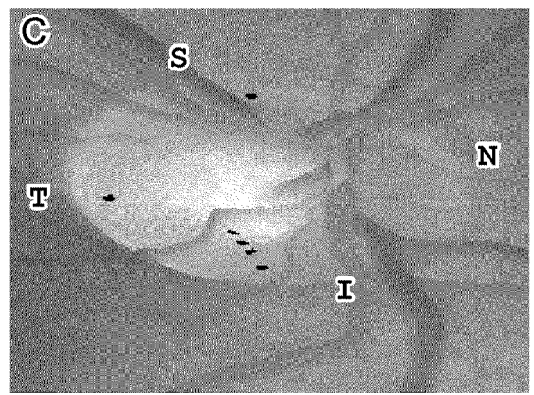

FIGS. 5A-5C depict in vivo images of a human optic disc collected with a ZFC, showing three ways of viewing the same optic disc image. FIG. 5A is a standard clinical photograph showing the optic disc surrounded by a portion of the retina. The photograph is labeled for orientation (superior (S), nasal (N), inferior (I), temporal (T)) and may be used to set minimum and maximum pixel values to span the dark and bright capabilities of the display. FIG. 5B is a grayscale image representing the tissue thickness computed pixel by pixel from two colors in the original color photograph, where thicker areas appear lighter and fiducial test points (i.e., 1, 2, 3, 4, 5, and 6) are located along three lines for image-to-image thickness comparisons as described further below. FIG. 5C is a three-dimensional, perspective rendering combining FIGS. 5A and 5B. While the 3D image can be rendered from any perspective, this one was selected to view the region of concern in glaucoma. In glaucoma, tissue thinning in this region may be observed as a darker shade (FIG. 5B) and a steeper slope (FIG. 5C). FIGS. 5B and 5C were processed from FIG. 5A using specialized software on a PC workstation.

The depths in the 3D image can be linear or non-linearly scaled. The computed depths are typically normalized to have values between 0 and 1, and the square root function provides a non-linear scaling that enhances thin areas and diminishes thicker areas. Texture mapping combines an enhanced 2D raw image with the 3D depths. Block 11 of FIG. 2 includes a table with point locations given as coordinates, angles, and clock times (in 15 minute increments), and the volume-related data given as raw values, intermediate, and computed values. The tabular data can also be displayed as shown in an x-y plot (FIG. 3) and bar chart (FIG. 4), etc. It may be possible to use histogram-related methods to enhance the raw or processed imagery, where the imagery can be converted to have the same appearance, format, and extracted fields as other current instruments.

With reference to FIG. 5B, a linear feature interpolation method according to an aspect of the present invention provides a way to repeatably locate points of interest in a featureless region of the image. This method allows registration of a fiducial point that can be used to locate it on multiple images. The method includes three steps: (1) identify points of interest (i.e., labeled 1, 2, 3, 4, 5, and 6 in FIG. 5B); (2) find line segments and percentages between distinct features that span the points of interest; and (3) apply the line segments and percentages to each image.

The linear feature interpolation processing according to an aspect of the present invention addresses an important and practical problem, namely that the regions of the optic disc of greatest interest in glaucoma have no surface details. For example, a point of interest may be located by placing the dots on visually distinct points on vessels. The line drawn between these two dots crosses an area devoid of surface detail but including the point of interest, which can be determined to reside at a particular percentage of the distance between the two dots. This method may also be used to co-register two or more images using the matching fiducial points in the images to develop a transformation that will allow images to be superimposed upon each other ("rubber sheeted"). Areas that have changed over time could be highlighted and possibly rendered in 3D using color to accentuate disc degradation. With respect to the concentric circles method described above, if the fiducial points are placed on visually distinct points on vessels as in the linear feature interpolation method, co-registration of images may also be possible. Using additional points inward from the four fiducial points on the outer edge of the optic disc may improve the co-registration and account for any distortion.

The anterior chamber angle is formed between the iris root and its junction with the cornea (clear, watch-crystal-like tissue) and the sclera (white of the eye). A water-like fluid, the aqueous humor, has its primary drainage route in the scleral part of that junction, through the trabecular meshwork to the canal of Schlemm. Increased resistance to aqueous outflow through the trabecular meshwork system is the cause of the elevated IOP in ocular hypertension and glaucoma. For over 100 years, studies of this pathway by progressively more sophisticated methods have not demonstrated a structural basis for the increased resistance. Adjacent to the trabecular meshwork is the ciliary body band, the beginning of a secondary route of aqueous outflow, the uveoscleral pathway. The surfaces of both the trabecular meshwork and of the ciliary body band are visualized clinically in the mirror in an examining contact lens, using the slit lamp. Therefore, the same spectral imaging techniques which are described herein for the optic disc may also be applied to other fundus tissues, the iris, the trabecular meshwork, and the ciliary body band.

Further, the system and method according to the present invention can be applied to and enhance the effectiveness of other instruments. One area of particular interest is OCT, which is so effective in the "wet" type of macular degeneration. OCT currently uses a single color laser, and using two more colors may provide additional processing options since the spectral techniques are so sensitive to the presence of blood, and the "wet" type is characterized by abnormal blood vessels, bleeding and/or leakage of fluid. In the other type of macular degeneration, the macula suffers thinning and atrophy. Each condition, together the leading cause of blindness, may produce a unique spectral signal.

While aspects of the invention have been illustrated and described, it is not intended that these aspects illustrate and describe all possible forms of the invention. It is understood that the features of various implementing aspects may be combined to form further aspects of the invention. The words used in the specification are words of description rather than limitation, and it is understood that various changes may be made without departing from the spirit and scope of the invention.

What is claimed is:

1. A system for determining a relative thickness of optic disc tissue, comprising:
   a light source configured to project broad spectrum light towards the optic disc tissue;
   a receiver configured to receive light reflected from the optic disc tissue at at least two spectral wavelengths;
   a digitizer in communication with the receiver configured to form a first image from the reflected light at each wavelength at a first time, and configured to form a second image from the reflected light at each wavelength at a second time; and
   a processor configured to
      determine a normalization point in each of the first and second images, compute a difference in the absorption of light by the optic disc tissue at selected image points in each image at each of the two spectral wavelengths to determine a thickness at each selected image point,
      determine relative thicknesses of the optic disc tissue of each image by compassing the thickness at each selected image point to the normalization point,
      compute an average of the relative thickness for each image to obtain an average thickness for each image,
      select one average thickness from the images to be a reference average thickness, and
      compute the difference between the average thickness and the reference average thickness for the first and second images to determine a relative thickness of the optic disc tissue over time.

2. The system according to claim 1, wherein the processor utilizes a mathematical model that assumes that the absorption of light by the optic disc tissue is an exponential function of the thickness of the optic disc tissue.

3. The system according to claim 1, wherein the selected image point is a single pixel in the image.

4. The system according to claim 1, further comprising a database for storing images and related data.

5. The system according to claim 1, further comprising a display for displaying the images.

6. A method for determining a relative thickness of optic disc tissue, comprising:
   illuminating the optic disc tissue with broad spectrum light with a light source;
   receiving light at a receiver reflected from the optic disc tissue at at least two spectral wavelengths;
   forming a first image from the reflected light at each wavelength with a digitizer at a first time, and forming a second image from the reflected light at each wavelength with the digitizer at a second time; and
   processing the image with a processor, wherein processing includes:
      determining a normalization point in each of the first and second images;
      computing a difference in the absorption of light by the optic disc tissue at selected image points in each image at each of the two spectral wavelengths to determine a thickness at each selected image point,
      determining relative thicknesses of the optic disc tissue of each image by comparing the thickness at each selected image point to the normalization point;
      computing an average of the relative thicknesses for each image to obtain an average thickness for each image;
      selecting one average thickness from the images to be a reference average thickness; and
      computing the difference between the average thickness and the reference average thickness for the first and second images to determine a relative thickness of the optic disc tissue over time.

7. The method according to claim 6, wherein determining the relative thicknesses includes relating the absorption of light by the optic disc tissue to the thickness of the optic disc tissue by an exponential function.

8. The method according to claim 6, wherein each selected image point is a single pixel in the image.

9. The method according to claim 6, further comprising storing images and related data.

10. The method according to claim 6, further comprising generating a grayscale image representing the tissue thickness from the formed image.

11. The method according to claim 10, further comprising generating a three-dimensional rendering combining the formed image and the grayscale image.

12. The method according to claim 6, further comprising identifying fiducial points of interest on the image, finding line segments between distinct features of the image that span the points of interest and the percentage along the line segment of the points of interest, and applying the line segments and percentages to another image to allow location of the points of interest on the other image for comparing the volume-related parameters between the images.

13. The method according to claim 6, further comprising displaying the image.

14. The method according to claim 6, further comprising using the determined relative thicknesses for assessing a glaucoma condition of an optic disc.

15. The method according to claim 12, wherein the fiducial points of interest are identified on an outer edge of an optic disc.

16. The system according to claim 1, wherein the processor is configured to compute a ratio of the absorption of light by the optic disc tissue at each selected image point at each of the two spectral wavelengths to determine a material property of the optic disc tissue at each selected image point.

17. The method of claim 6, further comprising computing a ratio of the absorption of light by the optic disc tissue at each selected image point at each of the two spectral wavelengths to determine a material property of the optic disc tissue at each selected image point.

\* \* \* \* \*